United States Patent [19]

Brunsting et al.

[11] Patent Number: 5,189,495
[45] Date of Patent: Feb. 23, 1993

[54] AMBIENT LIGHT SUPPRESSION FOR REFLECTANCE PHOTOMETERS

[75] Inventors: Albert Brunsting, Elkhart; Roger D. Sonnenburg, Osceola, both of Ind.

[73] Assignee: Miles Inc., Elkhart, Ind.

[21] Appl. No.: 754,065

[22] Filed: Sep. 3, 1991

[51] Int. Cl.[5] .................... G01J 3/51; G01N 21/47
[52] U.S. Cl. ................... 356/402; 250/226; 356/446; 359/892
[58] Field of Search ............. 356/402, 414, 416, 419, 356/445, 446; 250/226; 359/590, 580, 892

[56] References Cited

U.S. PATENT DOCUMENTS 4,655,712  4/1987  Croll ............................ 359/892 X
4,791,461  12/1988  Kishimoto et al. ................. 356/446

Primary Examiner—Vincent P. McGraw
Attorney, Agent, or Firm—Roger N. Coe

[57] ABSTRACT

A spectral cover for a reflectance photometer is disclosed in which the spectral cover is designed to cover the readhead area of the reflectance photometer and block the transmission of light in a wavelength range of at least 60 to no more than 200 nanometers centered about the detection wavelength while permitting light of other wavelengths to be transmitted. The invention permits the readhead cover to be permanently or semi-permanently positioned on the reflectance photometer. Since a user is able to see through the spectral cover it is possible to position a test device correctly and quickly over the readhead of the reflectance photometer. Signal noise levels due to ambient light are substantially eliminated by the invention.

4 Claims, 8 Drawing Sheets

5,189,495

AMBIENT LIGHT SUPPRESSION FOR REFLECTANCE PHOTOMETERS

FIELD OF THE INVENTION

This invention relates to means for suppressing ambient light in reflectance measuring instruments such as reflectance photometers. More particularly, the present invention relates to a spectral cover which blocks the transmission of light in a wavelength range of at least 60 nanometers (nm) to no more than 200 nm of the operating detection wavelength of a reflectance photometer while permitting light having other wavelengths to be transmitted.

BACKGROUND OF THE INVENTION

Instruments for measuring the reflectance of reagent test devices or reagent strips are well known. Such instruments typically measure the reflectance from a reagent pad of the test device or reagent strip in order to determine the presence and/or the amount of analytes, such as glucose, protein, ketone and the like, in body fluids. The reagent pad is a reagent impregnated area designed to react with a component (analyte) of a body fluid to provide a detectable change such as a color change. A color change can be measured by reflected light to provide a qualitative and/or quantitative indication of a particular analyte in the body fluid being tested.

Ambient light, i.e., light exterior to reflectance measuring instruments, can cause interference with the signal light of such instruments. Consequently, reflectance measurements are normally made inside reflectance measuring instruments where ambient light is blocked. Typically reflectance measuring instruments have an opaque door which is opened to allow placement of a test device or test strip. The door is then closed to block ambient light from the area where the reflectance measurement is made.

When a readhead door on a commercially available reflectance photometer is left open the measured reflectance can increase by at least 10% due to ambient light interference with the signal light. The affect of this is shown in FIG. 1 where a reflectance photometer is measuring glucose concentration ([G] in units of of milligrams per deciliter [mg/dL] of whole blood) as a function of measured reflectance. For example, when the reflectance changes from 0.250 reflectance units to 0.275 reflectance units (an increase of +10%) the reported result to the user changes from 116.1 to 89.5 mg/dL, which is a change of 23%. The required clinical accuracy of the whole system, including instrument, reagent pad, etc. must typically be less than 15%. It can be seen that a mere 10% increase in detected light level can result in inaccuracies of 23%, an amount which exceeds the clinical accuracy required for reflectance measuring instruments. It should also be noted that ambient light has more of an affect on [G] at different reflectance levels. This is particularly true at higher glucose readings.

In U.S. Pat. No. Des. 245,434 a reagent tray designed to hold a reagent test device is employed to transport a reagent test device into a reflectance photometer where reflectance measurements are made in an area substantially unaffected by ambient light.

In U.S. Pat. No. Des. 292,277, on the other hand, a more typical reflectance photometer is illustrated having a readhead door which is opened and closed. The readhead door is opened to insert a reagent test device and then closed prior to making a reflectance measurement. The closed door substantially prevents ambient light from interfering with the reflectance measurement. In order to remove the reagent test device from such a reflectance photometer it is necessary to again open the readhead door.

Notwithstanding the effectiveness of these approaches, neither of these prior procedures is attractive from the standpoint of user convenience, engineering simplicity and/or manufacturing costs. Customer convenience requires simple operating sequences with as few steps as possible. Another problem with the prior art procedures for suppressing or blocking ambient light is the fact that it is sometimes difficult to correctly position a reagent test device in an instrument because the final position of the reagent pad on the test device cannot be precisely determined when the reagent pad is inside the instrument upside down (facing the readhead window) and the door or lid to the reflectance measuring instrument is closed.

Accordingly, there is a need for means which simplify the positioning of a reagent test device or test strip in a reflectance photometer while simultaneously suppressing ambient light which will alter any measurement from its actual value. The present invention achieves these goals, eliminating the necessity for complex tray mechanisms to ratchet a reagent test device into a reflectance photometer for measurement and/or using a door or lid mechanism to suppress or prevent ambient light from interfering with reflectance measurements.

SUMMARY OF THE INVENTION

An object of the present invention is to provide simple and effective means for suppressing and/or eliminating ambient light in a reflectance photometer.

Yet another object of the present invention is to provide means attached to a reflectance photometer for suppressing and/or eliminating ambient light which do not require any movement of the means before, during or after making a reflectance measurement.

Another object of the present invention is to provide an inexpensive and effective means for visually aiding the positioning of a reagent pad on a reagent strip in the readhead area of a reflectance measuring instrument immediately prior to making a reflectance measurement.

In accordance with the present invention a spectral cover means is positioned over the readhead of a reflectance photometer. The spectral cover is designed to block the transmission of light which has a wavelength of at least 30 nm to no more than 50 nm of the operating detection wavelength while permitting light of other wavelengths to be transmitted. The spectral cover is so designed as to readily permit the insertion of a reagent test device into an open portion of the cover. Accordingly, no movement of the spectral cover is required for insertion or removal of a reagent test device. Since the spectral cover permits certain visible wavelength ranges to be transmitted a user can see through the spectral cover to correctly and conveniently position the reagent test device in the reflectance photometer over the readhead. The spectral cover thus eliminates ambient light problems, simplifies the operation of the reflectance photometer and reduces the cost of construction of the reflectance photometer.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Figure 1:
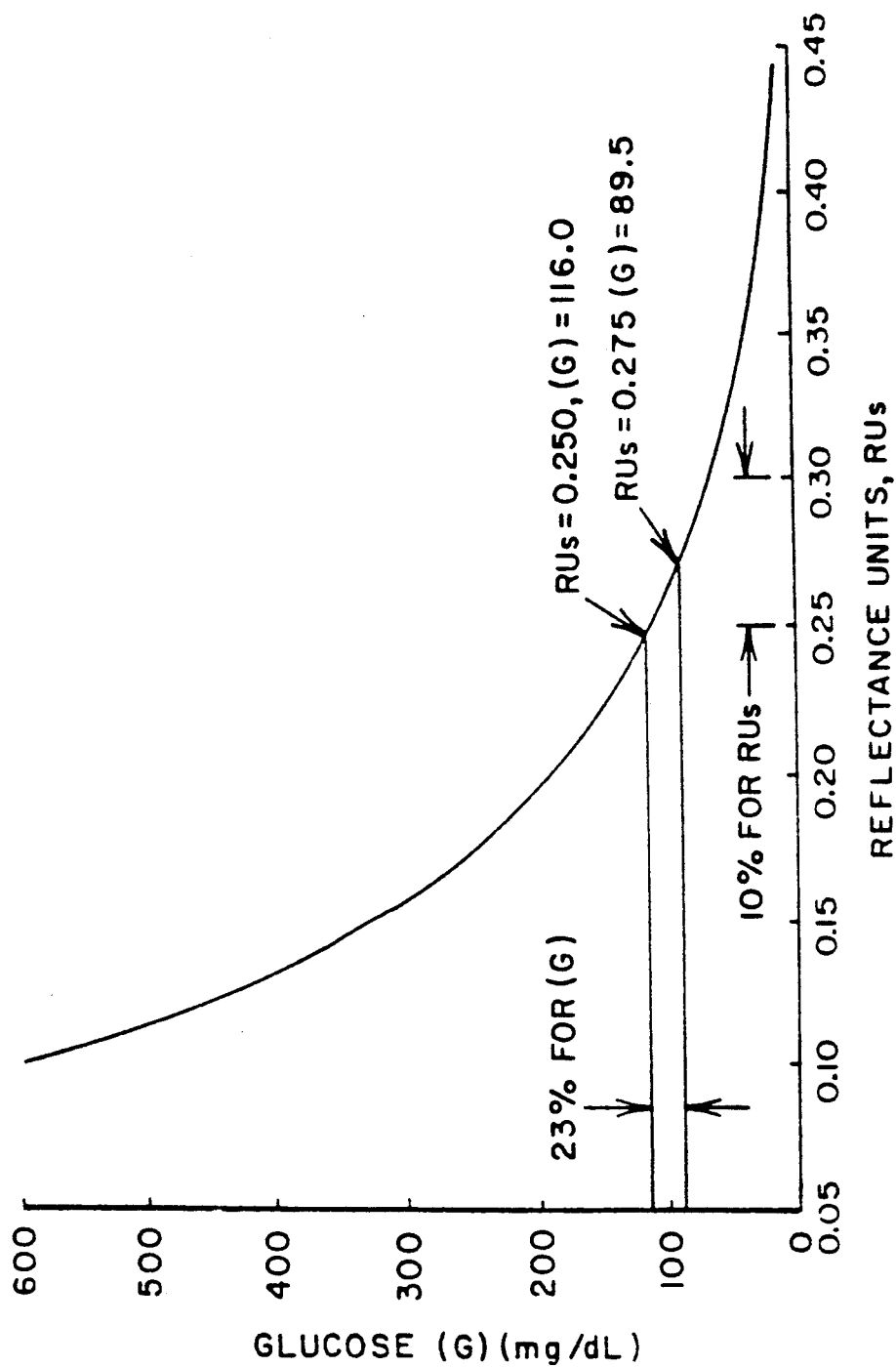
FIG. 1 is a graph showing the affects of a 10% ambient light level on glucose reflectance measurements in a reflectance photometer.

As seen in FIG. 1 ambient light is a source of optical noise which, unless suppressed, can significantly contaminate the photo-current from the detector of a reflectance photometer and cause inaccuracies in detection measurements reported by reflectance measuring instruments.

Figure 2:
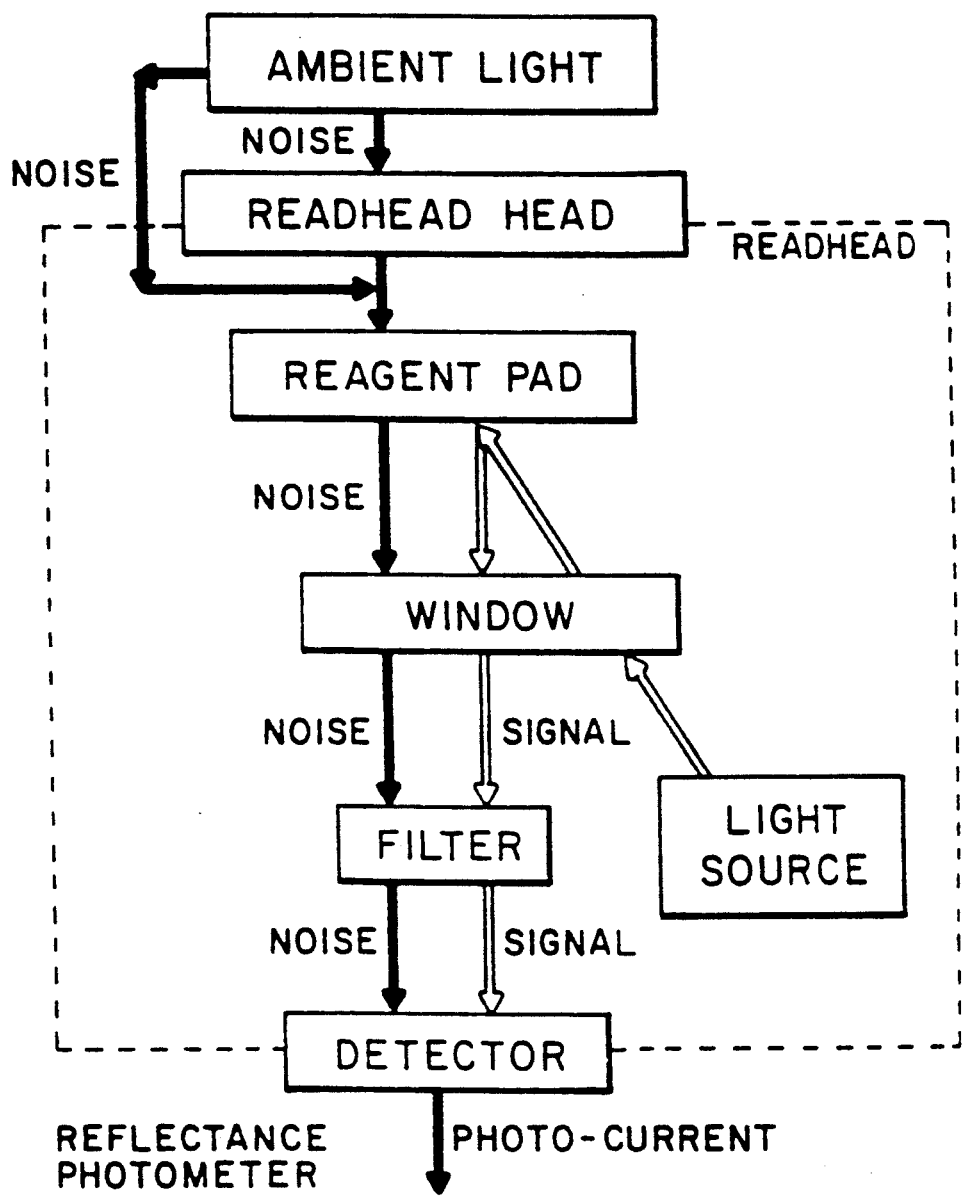
FIG. 2 is a flow chart illustrating signal and noise light paths inside a typical reflectance photometer.

FIG. 2 illustrates the signal and noise light paths of a typical reflectance photometer and shows where ambient light noise occurs. In a reflectance photometer light carrying the signal within the readhead starts at the light source, i.e., a LED, and is directed through the readhead window onto the reagent pad of a test means or test strip. Diffusely reflected light from the reagent pad passes through the same window and normally through a filter to the detector. Light carrying noise from ambient light conditions passes along a similar path as the signal light and additionally through the readhead door. The present invention suppresses the noise light caused by this ambient light so that it will have a negligible affect on the photo-current, and hence, the measurement reported to a user of a reflectance photometer.

Figure 3:
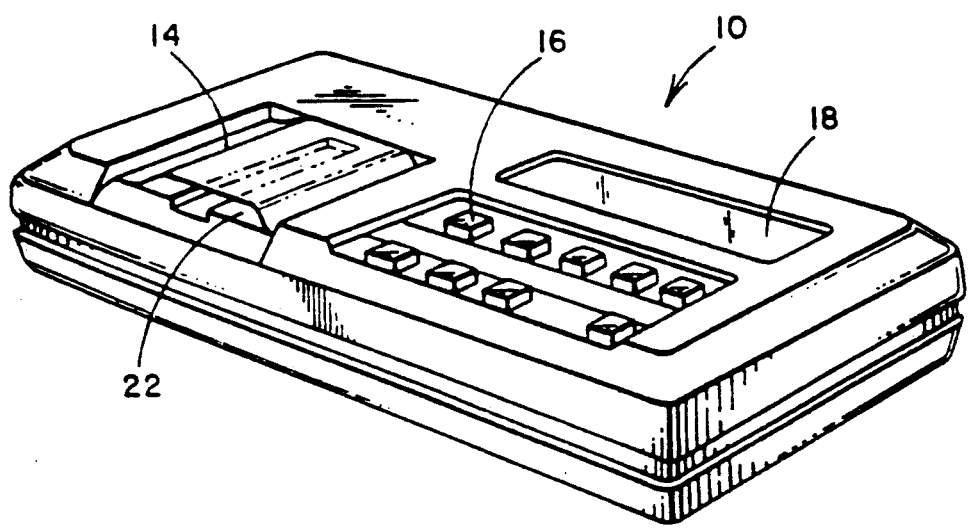
FIG. 3 is a diagrammatic perspective view illustrating a reflectance photometer with spectral cover of the present invention.
Figure 4:
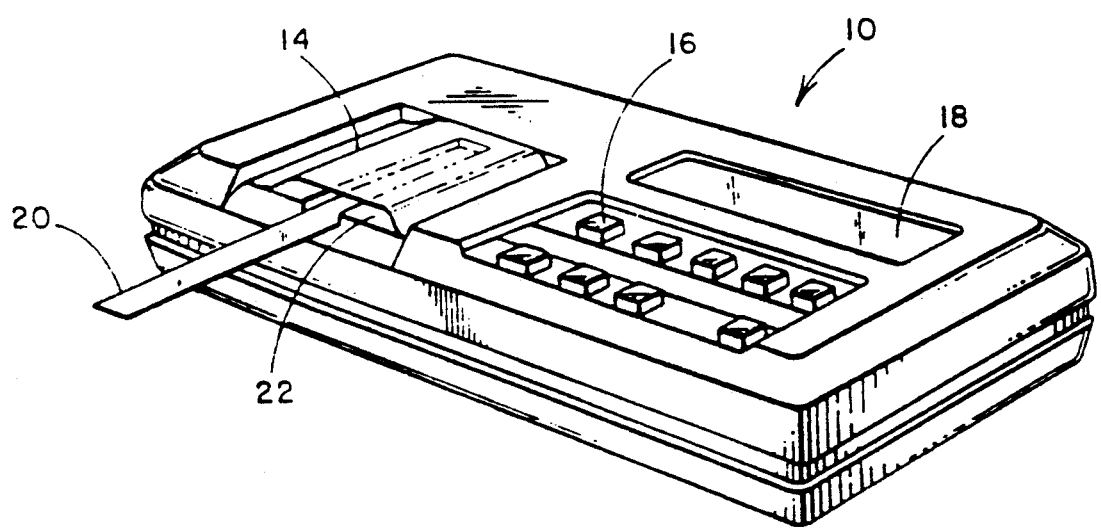
FIG. 4 is a diagrammatic perspective view of the reflectance photometer of FIG. 3 with a reagent strip inserted in position for making a reflectance measurement.

Referring now to FIGS. 3 and 4, these drawings illustrate spectral cover means in accordance with the present invention permanently or semipermanently attached to a reflectance photometer. Specifically, a reflectance photometer is shown generally at 10 comprising a readhead area 12 covered by a spectral cover 14. The reflectance photometer 10 has appropriate input keys or buttons 16 for input of specific information and a display window 18 for displaying instructional information and the results of any reflectance measurements which are made.

In FIG. 4 a reagent test device or test strip 20 is inserted into an opening 22 of the spectral cover 14. Spectral cover 14 is made from suitable plastic or glass material which permits certain visible wavelengths to be transmitted while blocking other wavelengths. It is important that the spectral cover suppress or block ambient light which has a wavelength range of at least 60 nm to no more than 200 nm, centered about the operating detection wavelength. When the center wavelength to be measured is approximately 710 nm it is therefore particularly important that the spectral cover block ambient light in the wavelength range from about 650 nm to about 770 nm. In some instances the spectral cover should suppress or block ambient light up to 100 nm of the detection wavelength. This is especially true where the light source used for detection is subject to abnormal variations in wavelength or the reflectance instrument is subject to temperature changes which affect the wavelength. For these special cases the spectral cover can be designed to block ambient light in the wavelength range of from about 610 nm to about 810 nm when the center wavelength to be measured is approximately 710. In either case the spectral cover permits the reagent test device 20 to be readily positioned over readhead 12 since a user is able to visually see where the reagent test device 20 is being positioned by looking through the spectral cover 14.

Since the spectral cover 14 is not required to move, i.e., it can be permanently or semipermanently positioned on the reflectance photometer, the resulting reflectance photometer is not only less expensive to manufacture but the resulting photometer is less prone to problems during use. This means that ultimately the entire reflectance photometer is more reliable since in normal operation the spectral cover does not have to be moved or adjusted by the user. It may be desirable, however, to construct the spectral cover with a hinge to permit a user to periodically clean any contamination in the readhead area surrounding the window of the reflectance photometer. Alternatively, the spectral cover can be constructed in such a manner to snap into place for ease in removing the spectral cover when cleaning is necessary or desirable.

The nature of the spectral cover permits the correct positioning of a reagent test device and, more particularly a reagent pad, over the optical readhead of the reflectance photometer since the reagent test device can be visually positioned laterally and in terms of depth to assure the correct location of the test device before measurement. In addition, the user can see if the reagent test device has been correctly inserted into the reflectance photometer relative to the downward positioning of the reagent pad to be measured.

While the spectral cover 14 has been shown in FIGS. 3 and 4 as having an opening at one end for the insertion of a reagent strip 20 into the readhead area 12 of reflectance photometer 10 it should be understood that spectral cover 14 could be designed to have an opening (not shown) along one side of the cover which would permit the introduction of a reagent strip via the side of the spectral cover into the readhead are.

Thus the spectral cover allows the user of a reflectance photometer to easily insert a reagent pad on a test means or test strip into a readhead of the reflectance photometer; allows the user to visually see that the reagent pad is positioned correctly; allows the user to see that there is no contamination near the reagent pad; and suppresses the ambient light for wavelengths outside the desired signal wavelength range.

Figure 5:
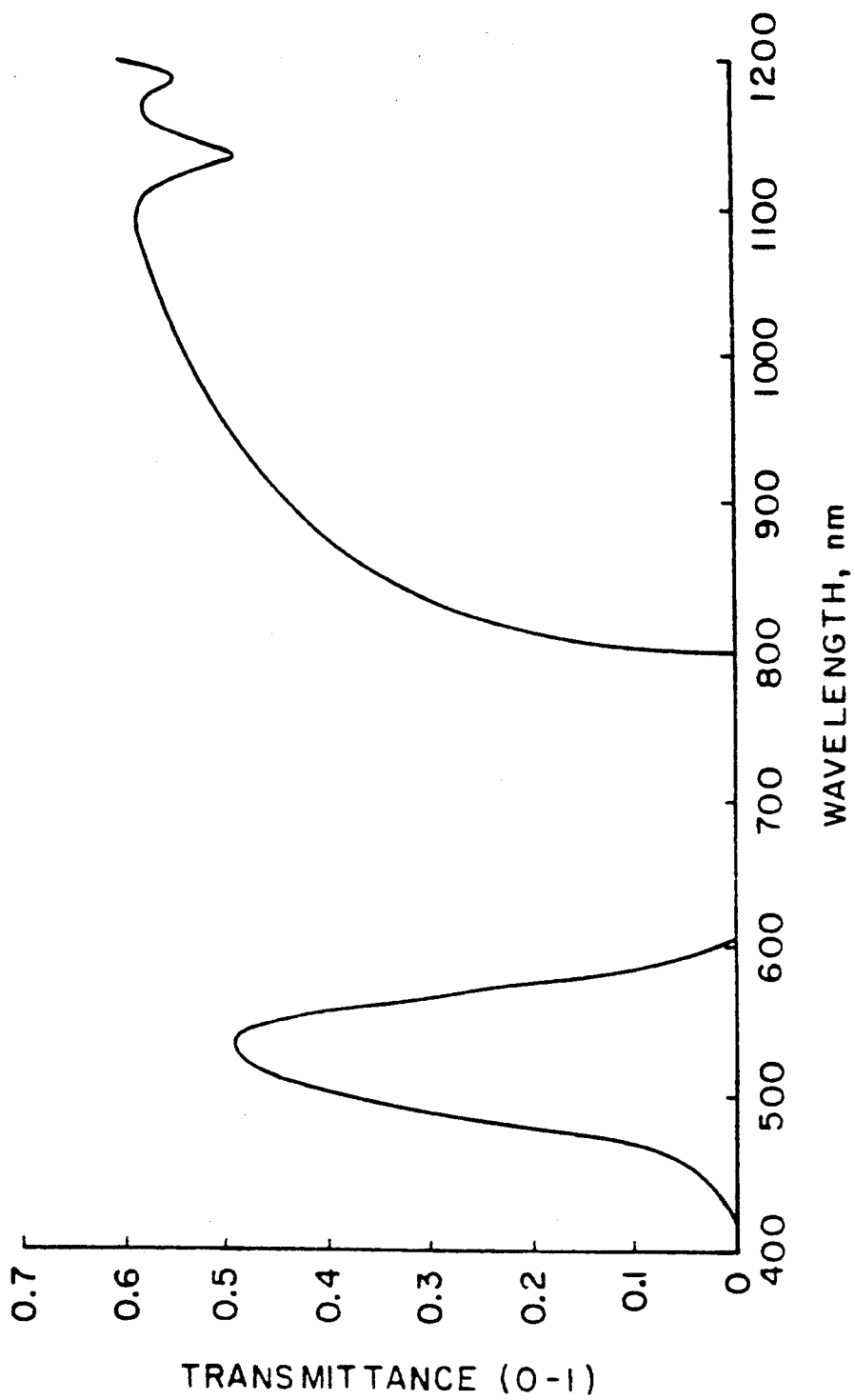
FIG. 5 is a graph showing the spectral transmission of a spectral cover.
Figure 6:
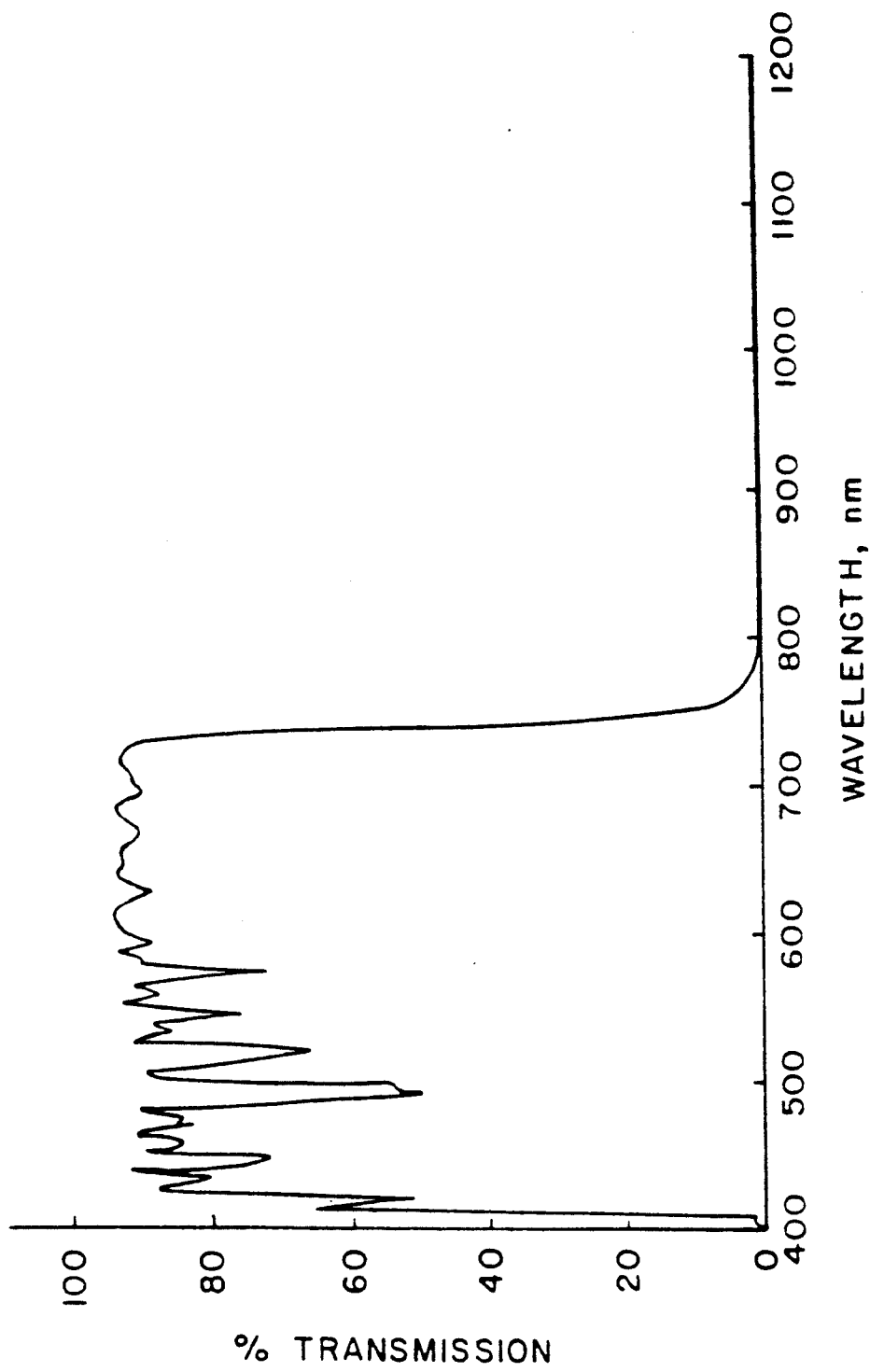
FIG. 6 is a graph showing a scan of an IR cutoff filter.

The nature of the material used for the construction of the spectral cover is not critical provided it is reasonably durable and has the wavelength transmission characteristics mentioned above. For example, GE Lexan 2148 and a polycarbonate (Makrolon 2401) are suitable materials which can be used for the construction of the spectral cover. These colored plastic materials pass light in the visible range and in the near infrared (IR) from 800 to 1200 nm (nm). See FIG. 5. Light in the 800 to 1200 nanometer range can be blocked by a filter such as a filter made from all dielectric thin films. See, for example, A. Brunsting et al, Applied Optics, Vol. 25, No. 18, "Environmental Effects on All-Dielectric Bandpass Filters," Sep. 15, 1986. The result of using such a filter is illustrated in FIG. 6. If desired a more expensive version of such a filter can be used to block visible (400 to 600 nm) light.

Figure 7:
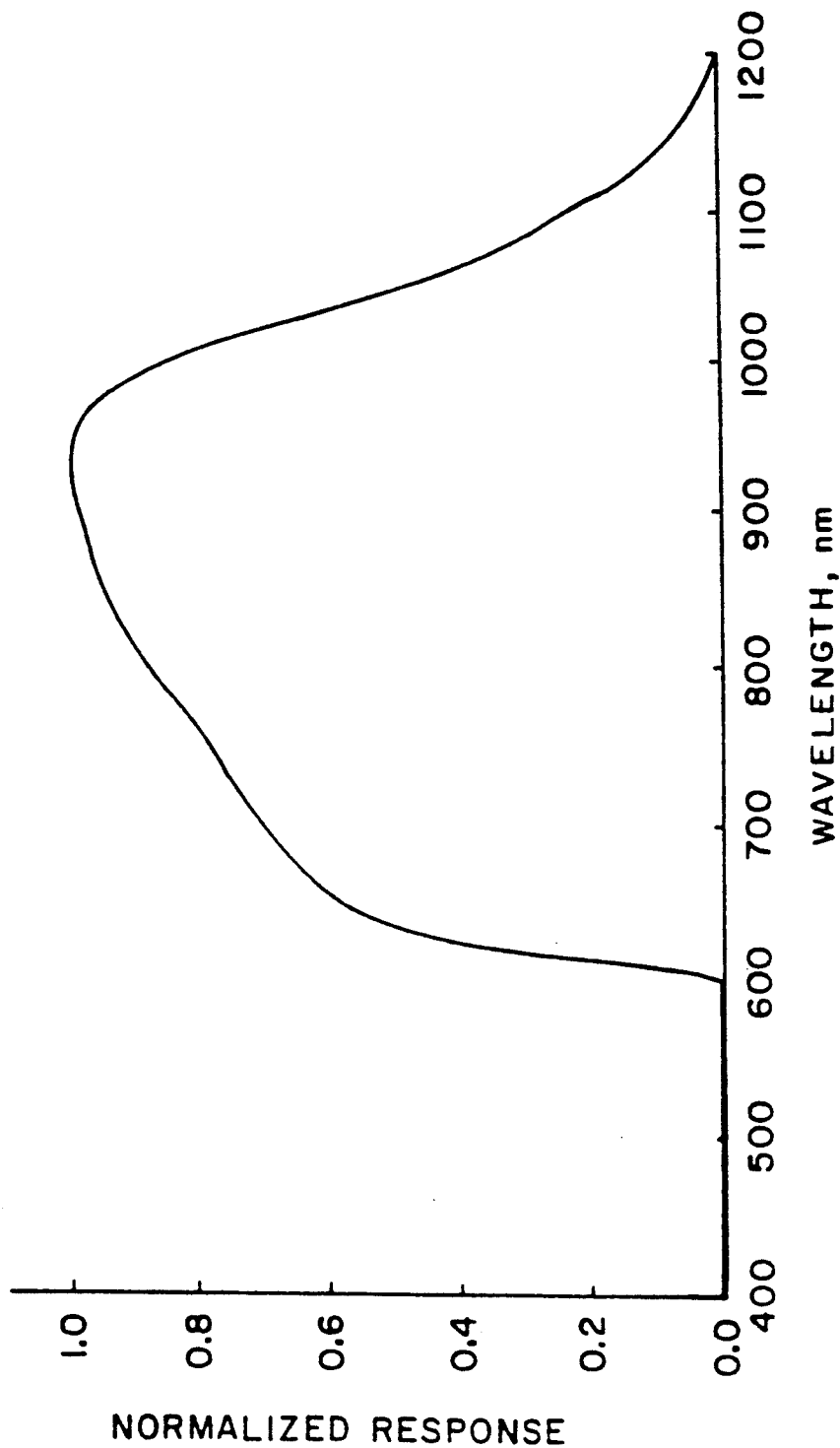
FIG. 7 is a graph showing a spectral response scan of a typical detector.

It is also possible to encapsulate the detector in a colored material which suppresses the visible portion of the ambient light passing through the spectral cover. (See FIG. 7.)

Figure 8:
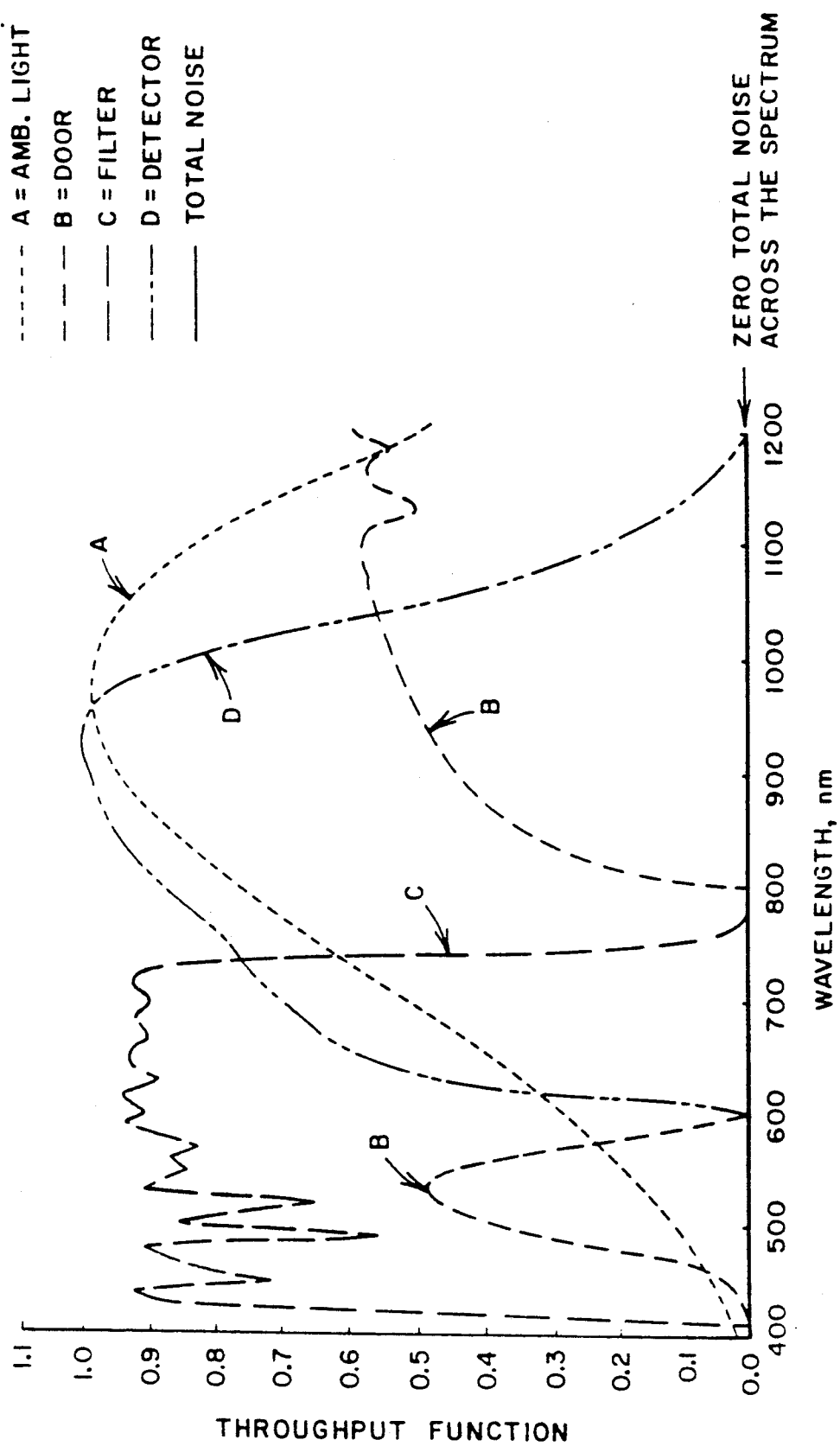
FIG. 8 is a graph showing the spectral throughputs for optical noise due to ambient light.

By using all of these blocking effects the spectral throughput for optical noise due to ambient light can be as shown in FIG. 8 where an ambient light source with a color temperature of about 2900 degrees Kelvin is plotted. The cumulative blocking in all three spectral regions is shown by a zero throughput function at the bottom of the plot. The throughput function at a given wavelength is the product of the ambient light, readhead door, filter(s), and detector at that wavelength. The total effect of the noise on the detector's photo-current is the integration of the throughput function for noise over all wavelengths for which the detector is sensitive.

Figure 9:
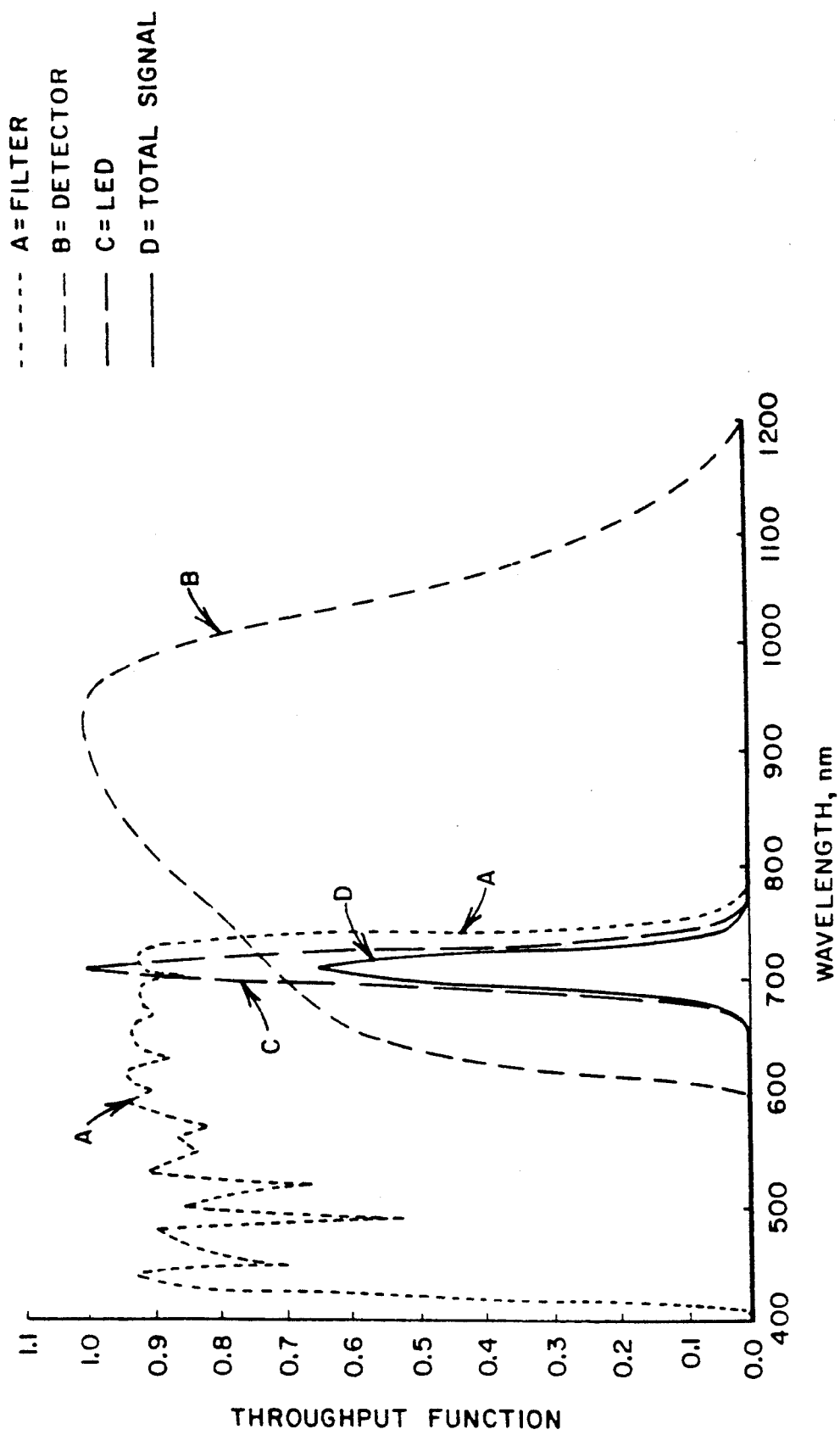
FIG. 9 is a graph showing the spectral throughputs for the optical signal in a reflectance photometer according to the present invention.

Because of the measurement to be made signal light within the desired range must pass through the filter(s) and through the detector onto the detector's photo-sensitive surface. This is shown in FIG. 9 where one can see a significant D curve, i.e., total signal, computed in the same way as the noise throughput function. Thus, the total effect of the signal on the detector's photo-current is the integration of the throughput function for signal over all wavelengths for which the detector is sensitive. The signal is allowed through while the noise is suppressed.

From the foregoing, it will be seen that this invention is well adapted to attain all of the ends and objects heretofore set forth, together with other advantages which are obvious and inherent. The unique spectral cover provides a simple and effective means for suppressing ambient light in a measuring area of a reflectance photometer with permitting the visual positioning of a reagent strip. Since no movement of the spectral cover is needed during the insertion and removal of a reagent pad from the readhead area there is one less moving part on the reflectance photometer which can cause operating problems. As a result of this and the correct positioning of reagent test devices the overall reliability of the reflectance photometer is substantially improved while the overall operation of the reflectance photometer is substantially simplified.

Obviously, many modifications and variations of the invention as heretofore set forth can be made without departing from the spirit and scope thereof and therefore only such limitations should be imposed as are indicated by the appended claims.

What is claimed is:

1. A reflectance photometer for making reflectance measurements from a reagent test device wherein said reflectance photometer has a readhead area covered with a spectral cover which blocks the transmission of light in the range of at least 60 nanometers but no more than 200 nanometers centered about the operating detection wavelength from entering said readhead area and in which the spectral cover does not have to be moved during use for the insertion and removal of a reagent test device into and from said readhead area.

2. The reflectance photometer of claim 1 in which the spectral cover is a colored plastic.

3. The reflectance photometer of claim 2 in which the colored plastic is polycarbonate.

4. The reflectance photometer of claim 1 in which the operating detection wavelength is 710 nanometers.

* * * * *